United States Patent [19]

Kawakami et al.

[11] Patent Number: 4,634,575

[45] Date of Patent: Jan. 6, 1987

[54] AUTOMATIC CUVETTE LOADING APPARATUS

[75] Inventors: Kazuo Kawakami; Yawara Nagai; Takayuki Aihara, all of Hachioji, Japan

[73] Assignee: Olympus Optical Co., Ltd., Tokyo, Japan

[21] Appl. No.: 771,484

[22] Filed: Sep. 3, 1985

Related U.S. Application Data

[63] Continuation of Ser. No. 434,109, Oct. 13, 1982, abandoned.

[51] Int. Cl.⁴ .......................... G01N 35/04; B65H 1/26
[52] U.S. Cl. ........................................ 422/63; 221/198;
    221/226; 414/119; 414/417; 422/64; 422/65;
    422/102; 422/104
[58] Field of Search ...................................... 422/63–65,
    422/67, 102, 104; 414/114, 417; 221/197, 198,
    226

[56] References Cited

U.S. PATENT DOCUMENTS

| 3,180,499 | 4/1965 | Wildheim et al. | 414/119 |
| 3,609,047 | 9/1971 | Marlow | 250/218 |
| 4,039,286 | 8/1977 | Keller et al. | 422/67 |
| 4,058,367 | 11/1977 | Gilford | 422/67 |
| 4,194,647 | 3/1980 | Spurrier | 221/197 |
| 4,308,231 | 12/1981 | Kolber | 422/64 |
| 4,338,279 | 7/1982 | Orimo et al. | 422/67 |
| 4,456,580 | 6/1984 | Yamada et al. | 422/63 |
| 4,476,733 | 10/1984 | Chlosta et al. | 422/64 |

FOREIGN PATENT DOCUMENTS

56-132565  10/1981  Japan .................................. 422/104

Primary Examiner—Michael S. Marcus
Attorney, Agent, or Firm—Parkhurst & Oliff

[57] ABSTRACT

A cuvette for use in an automatic chemical analyzer is formed of molded transparent plastic material, the cuvette having a flat box construction made of main walls, side walls and a bottom. Entrance and exit windows for a measuring light beam are formed in the side walls in such a manner the windows are recessed inwardly with respect to the side walls. A number of such cuvettes are arranged in a magazine and a plurality of such magazines are set in an automatic cuvette loader for supplying the cuvettes in a reaction line one by one. The automatic cuvette loader has a first slider for moving the magazines stocked in a container into a cuvette loading position one by one and for pushing the cuvettes in the magazine in a direction perpendicular to a discharging direction and a second slider for pushing a cuvette array in the cuvette discharging direction so as to discharge the cuvettes one by one through an outlet formed in the magazine.

11 Claims, 9 Drawing Figures

AUTOMATIC CUVETTE LOADING APPARATUS

This is a continuation of application Ser. No. 434,109 filed Oct. 13, 1982, abandoned.

BACKGROUND OF THE INVENTION

1. Field of the Invention

The present invention relates generally to chemical analysis, and more particularly to a cuvette for use in colorimetric analysis, a cuvette magazine containing a number of cuvettes therein and a cuvette auto-loading apparatus for supplying the cuvettes into a reaction line of an automatic analyzer in succession.

2. Description of the Prior Art

There have been proposed various types of automatic chemical analyzers. In a colorimetric analyzer, a sample such as a serum and a reagent are delivered into a reaction vessel fed along a reaction line to form a test liquid and then the light absorption of the test liquid is photometered to effect a quantitative analysis. Such analyzers may be classified into direct measuring systems in which the test liquid contained in the reaction vessel is photometered and indirect measuring systems in which the test liquid is transferred from the reaction vessel into a flowcell and the test liquid in the flowcell is photometered. From the view-point of construction of the analyzer, the former system is superior to the latter system, because the construction can be made much simpler in the former system. As to the treatment of the reaction vessel, there are two systems. In the first system the reaction vessels travelling along the reaction line are used repeatedly, while in the second system new reaction vessels are fed successively into the reaction line. In the first system a mechanism must be provided for washing and drying the reaction vessels, so that the whole apparatus is liable to be complicated in construction, large in size and expensive. Further, the first system requires a great amount of a washing liquid and a problem occurs in treatment of waste washing liquid. If the washing is not effected sufficiently, contamination may occur between successive test liquids, which affects the accuracy of measurement. Moreover, while the reaction vessels are used repeatedly, they are liable to be injured or scratched and therefore the measuring accuracy might be decreased. Contrary to this, in the second system the above problems can be entirely removed, because the reaction vessels which have been once used are discharged. However, an automatic vessel loader must be arranged for supplying new reaction vessels into the reaction line. Known automatic reaction vessel loaders have several drawbacks including that they are of complicated construction and require very cumbersome treatment. Particularly, when the reaction vessels are held by hands, finger-prints might be applied on the reaction vessels. Further, the known, auto-loaders do not work positively and reliably and often fail to feed the reaction vessels in the reaction line in a correct order.

As explained above, in the known chemical analysis, in order to effect a precise analysis the reaction vessels must be handled very carefully not to be stained or injured. In the known analyzer of the direct measuring type use is made of reaction vessels comprising a test tube or a box-shaped cuvette. In these test tubes and cuvettes, the entrance and exit windows for a measuring light beam are directly exposed to the outside and thus are liable to be stained and injured. Further, disturbing stray lights are liable to impinge upon the cuvette to decrease the measuring accuracy.

Moreover, in the known auto-loaderd, it is quite cumbersome to charge or set the reaction vessels or cuvettes into the auto-loader. This operation requires a long time and the analysis has to be interrupted during the charging operation.

SUMMARY OF THE INVENTION

The object of the present invention is to provide a novel and useful apparatus for automatically feeding successive cuvettes into a reaction line in a positive and reliable manner.

It is another object of the invention to provide an automatic cuvette loading apparatus which can feed successive cuvettes into a reaction line without staining and injuring the cuvettes.

It is still another object of the invention to provide an automatic cuvette loading apparatus which has a simple construction and can be made inexpensively.

According to the invention, an automatic cuvette loading apparatus for use in an automatic chemical analyzer comprises means for containing a plurality of magazines each containing a plurality of cuvettes;

means for successively feeding the magazines from the magazine containing means into a cuvette loading position;

means for successively loading the cuvettes contained in a magazine situated at the cuvette loading position into a reaction line of the analyzer; and means for removing an empty magazine from the cuvette loading position.

The present invention also relates to a cuvette for use in a chemical analyzer of the direct measuring type and has for its object provision of a cuvette which can be effectively protected against stain, injury and stray light.

According to the invention, a cuvette for use in an automatic chemical analyzer comprises first and second main walls arranged in parallel with each other, first and second side walls arranged between the first and second main walls at their side edges in parallel with each other, a bottom arranged between the first and second main and side walls at their bottom edges, and entrance and exit windows provided in the first and second side walls, respectively, in parallel with each other, said entrance and exit windows being recessed inwardly with respect to the side walls, and the side edges of the main walls.

This invention further relates to a magazine for containing a number of cuvettes for use in a chemical analyzer and has for its object provision of a novel and useful cuvette magazine which can contain a number of cuvettes, while the cuvettes can be protected against stain and injury.

It is another object of the invention to provide a cuvette magazine which contains a number of cuvettes in such a manner that the cuvettes can be discharged successively out of the magazine in a positive and reliable manner.

It is still another object of the invention to provide a cuvette magazine which can be simply set in an automatic cuvette loading apparatus.

According to the invention, a magazine for containing a plurality of cuvettes for use in an automatic chemical analyzer comprises a top and a bottom arranged in parallel with each other, first and second side walls arranged between opposing side edges of the top and bottom in parallel with each other, third and fourth side walls arranged between the other opposing side edges of the top and bottom in parallel with each other, and an outlet provided in the first side wall for discharging the cuvettes therethrough one by one.

DESCRIPTION OF THE PREFERRED EMBODIMENTS

Figure 1:
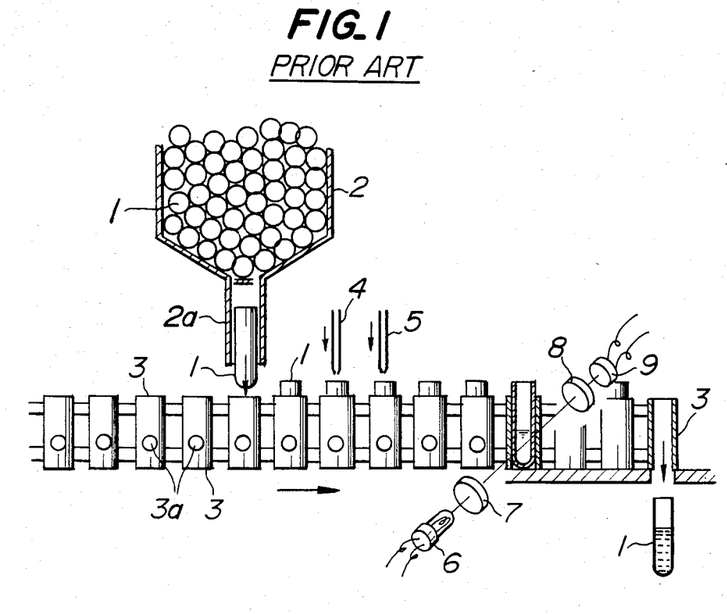
FIG. 1 is a schematic view showing a known chemical analyzer of a direct measuring type using test tube type cuvettes.

FIG. 1 shows schematically a known chemical analyzer in which reaction vessels are used only once and used vessels are disposed of a number of reaction vessels in the form of test tubes 1 are set in an automatic loader 2. Below the loader 2 is arranged a mechanism for rotating the test tubes 1 by an angle of 90° so that the test tubes fall down one by one via a tube 2a. Underneath the tube 2a is arranged a reaction line comprising a chain of holders 3 and a mechanism for moving the chain rightward. After a test tube 1 has been inserted into a holder 3, a given amount of a sample is delivered to the test tube 1 by means of a sample delivery nozzle 4 and then a given amount of reagent is delivered to the test tube by means of a reagent delivery nozzle 5. While the test tube 1 is fed further rightward, these liquids react with each other to form a test liquid. When the test tube 1 arrives at a measuring station, a light beam emitted from a lamp 6 and collimated by a lens 7 is made incident upon the test tube 1 via an opening 3a formed in the holder 3. The light beam transmitted through the test liquid is received by a light detector 9 by means of a filter 8 to measure the absorption of the test liquid. After the measurement, the test tube 1 containing the test liquid drops down from the holder 3. In this manner, successive samples can be tested, while new test tubes 1 are successively supplied into the reaction line.

In the above explained automatic chemical analyzer, it is quite cumbersome to charge new test tubes in the auto-loader 2 and during this treatment the test tubes are liable to be stained by finger-prints as well as to be injured. This results in decreased measuring accuracy. Further, in the auto-loader 2, the test tubes 1 are easily injured by rubbing against. Moreover, the test tubes 1 are liable to be clogged in the auto-loader 2 and thus, the test tubes can not be fed positively into the holders 3 one by one.

Figure 2:
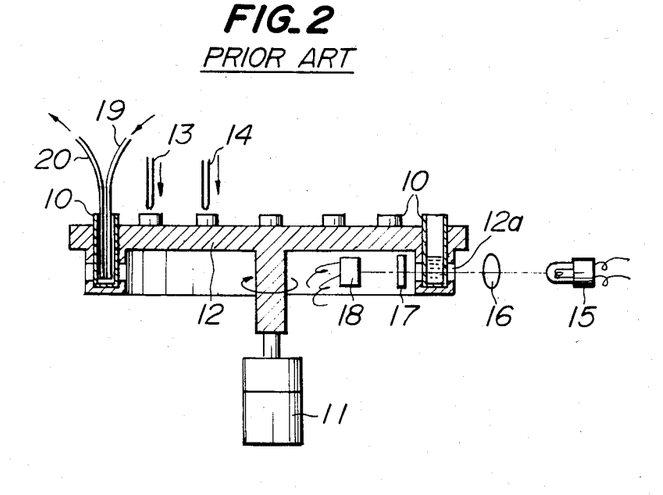
FIG. 2 is a schematic cross section illustrating a known chemical analyzer in which cuvettes are repeatedly

FIG. 2 shows schematically a known chemical analyzer in which reaction cells are used repeatedly. A number of reaction cells 10 are provided in a turntable 12 along its periphery and the turntable is rotated intermittently by a motor 11 at a given frequency. Given amounts of sample and reagent are delivered into a reaction cell 10 by means of sample and reagent delivery nozzles 13 and 14, respectively, to form a test liquid therein. After a given time period, the test liquid is photometered at a measuring station. In the measuring station a light beam emitted from a lamp 15 and collimated by a lens 16 is made incident upon the cell 10 via an opening 12a formed in the turntable 12 and the light flux transmitted through the cell 10 is received by a light detector 18 via a filter 17. At the measuring station, the absorbance of the test liquid contained in the reaction cell 10 is measured. After the measurement, the cell 10 is fed into a washing station at which the test liquid is first sucked out by means of a sucking nozzle 20, a washing liquid is poured into the cell 10 by means of a delivery nozzle 19 and finally the washing liquid is sucked out by the nozzle 20. The above operations are repeated a desired number of times to wash the cell to the desired extent. Since the sucking nozzle 20 must be inserted into the reaction cell to its bottom in order to discharge the liquid, a mechanism must be provided for moving the nozzle up and down over a relatively long distance. After the washing, residual washing liquid in the cell 10 is removed by, for example, jetting a heated air stream against the cell, as the case may be.

In the known chemical analyzer shown in FIG. 2, it is necessary to provide mechanisms for discharging the test liquids from the reaction cells, and for washing and drying the reaction cells, so that the apparatus is liable to be complicated, large and expensive. Further, it is quite cumbersome to control the operational timings of the various mechanisms. In particular in order to avoid contamination between successive test liquids, it is necessary to effect a sufficient washing, which requires a greater amount of the washing liquid and thus, it is difficult to treat a greater amount of the waste washing liquid. Moreover, a relatively long washing time is required for effective washing. The operational timings of the analyzer must be latched to the long washing time and, thus, the treating speed is lowered.

The present invention avoids the drawbacks of the known chemical analyzers by providing a novel and useful cuvette type reaction vessel having a special construction.

Figure 3:
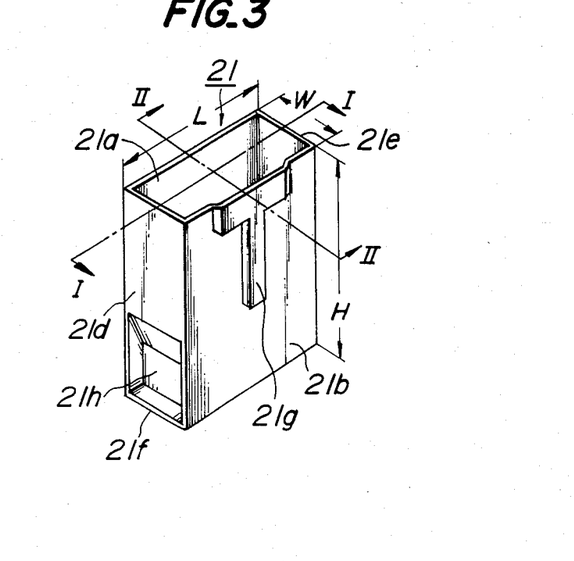
FIGS. 3, 4A and 4B are perspective and cross sectional views depicting one embodiment of a cuvette according to the present invention.
Figure 4A:
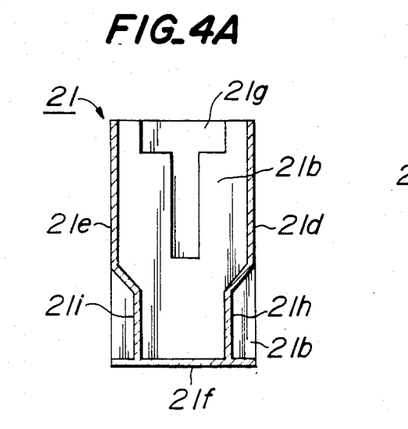
Figure 4B:
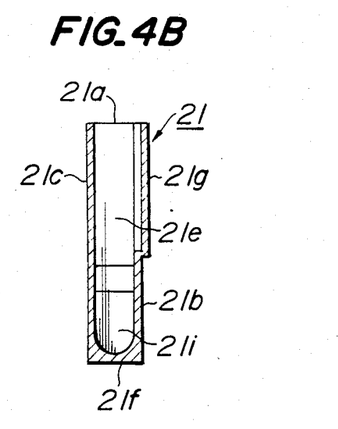

FIG. 3 is a perspective view showing an embodiment of a cuvette type reaction vessel according to the present invention and FIGS. 4A and 4B are cross sections cut along lines I—I and II—II in FIG. 3, respectively. In the present embodiment, the cuvette 21 is formed of a molded transparent synthetic resin and has a generally flat box shape. The cuvette 21 has an opening 21a at its top, two main walls 21b and 21c, two side walls 21d and 21e and a bottom 21f. In one of the main walls 21b there is formed a T-shaped projection 21g which serves to hold the cuvette in a cuvette holder due to its elastic force as will be explain later. The side walls 21d and 21e of the cuvette are arranged perpendicularly to a measuring optical axis and include entrance and exit windows 21h and 21i for a measuring light beam. As best shown in FIG. 4A, the windows 21h and 21i are recessed inwardly with respect to the side walls 21d and 21e, respectively, and the side edges of the main walls. That is to say, the measuring windows 21h and 21i are surrounded by the main walls 21b and 21c and the bottom 21f and therefore the windows are protected effectively against stain and injury, which ensures a high measuring accuracy. Further, the inner surface of the bottom 21f is formed semicylindrically so that the photometry can be carried out with a very small amount of the test liquid.

Figure 5:
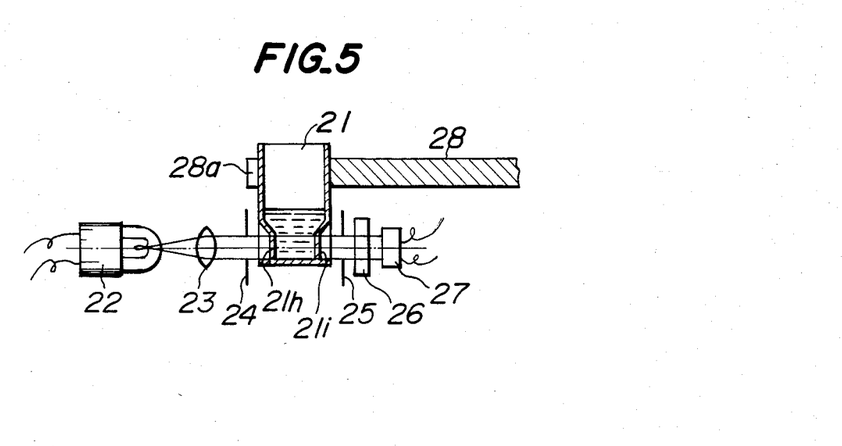
FIG. 5 is a schematic cross section illustrating a photometering device using a cuvette according to the present invention.

FIG. 5 shows an embodiment of a photometering station in which the absorbance of the test liquid contained in the cuvette 21 is measured. A light beam emitted from a lamp 22 is collimated by a lens 23 and is made incident upon the entrance window 21h of the cuvette 21 through a stop 24. The light flux emanating from the exit window 21i is made incident upon a light detector 27 through of a stop 25 and an optical filter 26. The cuvette 21 is held in a recess 28a formed in a turntable 28 at its periphery due to the elasticity of the cuvette.

Figure 6:
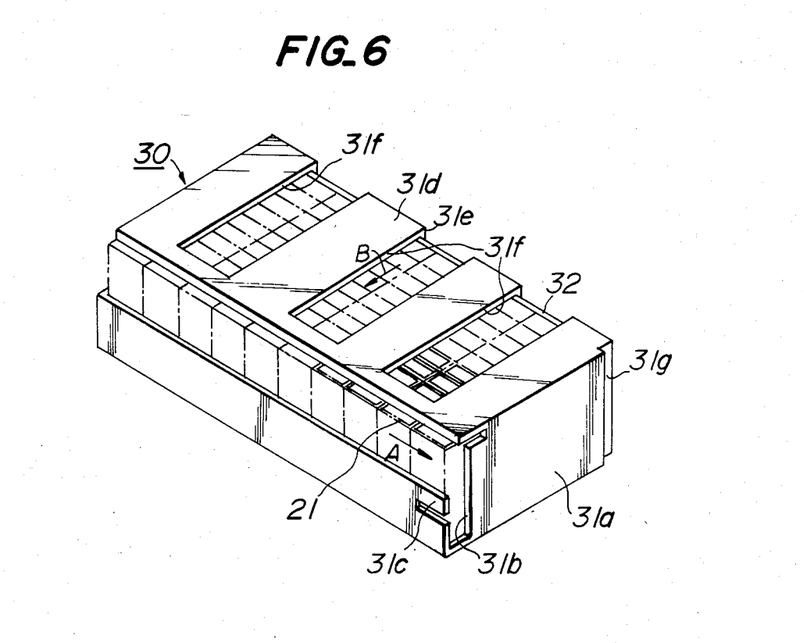
FIG. 6 is a perspective view showing an embodiment of a cuvette magazine according to the present invention.

According to the invention, a large number of cuvettes 21 are arranged in a magazine 30 as illustrated in FIG. 6. It is not necessary at all for an operator of the analyzer to insert the cuvettes in the magazine, but the magazine having the cuvettes contained therein is available. Therefore, the cuvettes can be further protected against stain and injury. The magazine 30 may be formed by a molded plastic or metal. In the present embodiment, the magazine has such a length viewed in a direction A that ten cuvettes are arranged side by side and such a width measured in a direction B that also ten cuvettes are arranged side by side. Therefore, the magazine can contain a hundred cuvettes in a matrix form. In a side wall 31a of the magazine 30 is an outlet 31b having a width which is substantially equal to the width W of the cuvette 21 and a height which is nearly equal to the height H of the cuvette 21. In order to ensure that the cuvette 21 can be discharged out of the magazine 30 through the outlet 31b in a correct posture, a resilient strip 31c is formed in a front wall of the magazine at a portion adjacent to the outlet 31b by providing a recess in the wall. In top and bottom walls 31d and 31e of the magazine are formed three recesses 31f. It should be noted that the recesses 31f do not extend in the upper wall 31d up to the front edge so that the cuvettes in a first column are not situated under the recesses. This ensures the smooth movement of the cuvettes. A push plate 32 is inserted in the magazine between the assembly of the cuvettes and the rear wall 31e. As will be explained hereinafter, the cuvette array may be moved in the direction B by moving the plate 32 in this direction B. Along a right hand side edge of the side wall 31a is formed a step 31g which avoids an inverse insertion of the magazine into an automatic cuvette loader having a corresponding projection.

Figure 7:
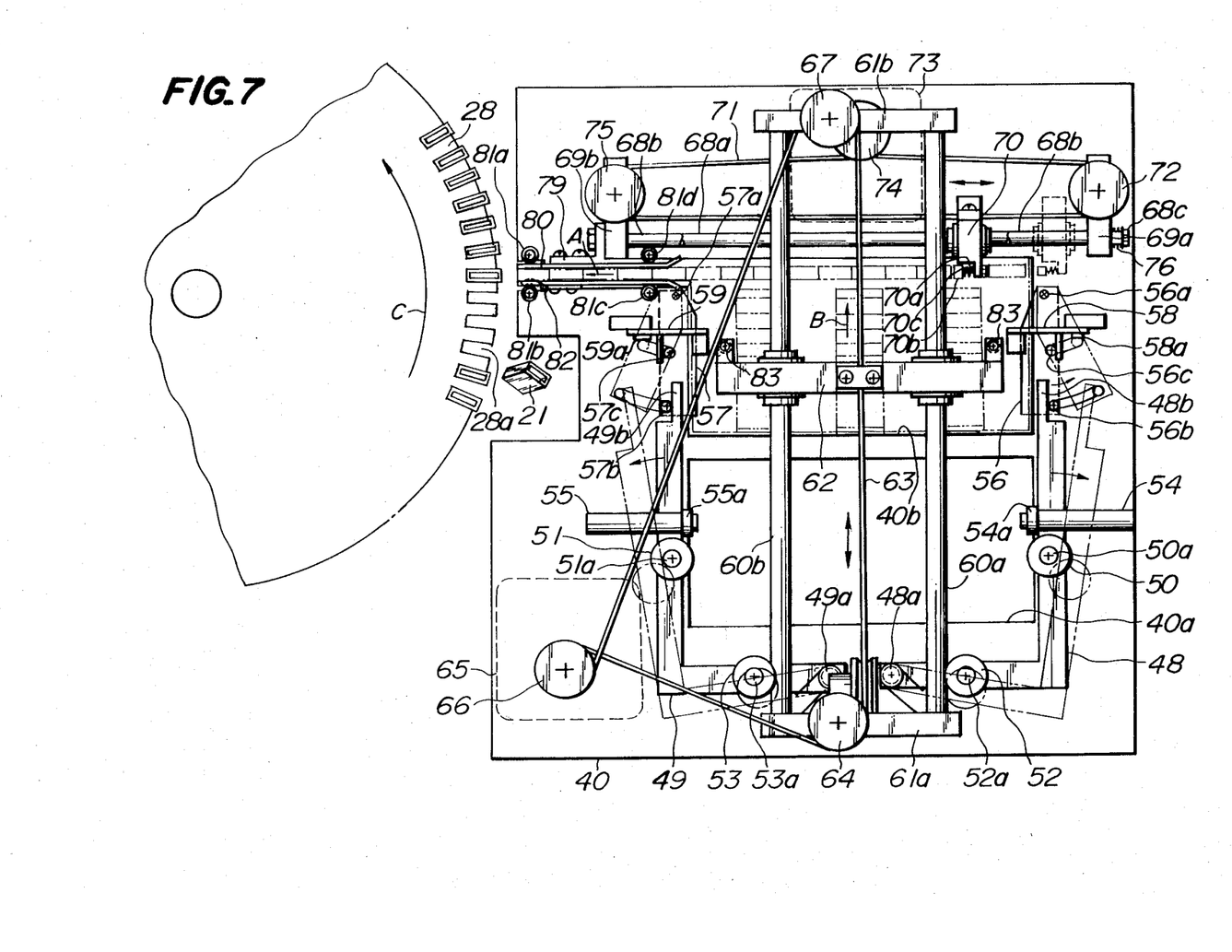
FIG. 7 is a plan view depicting an embodiment of an automatic cuvette loading apparatus according to the present invention.
Figure 8:
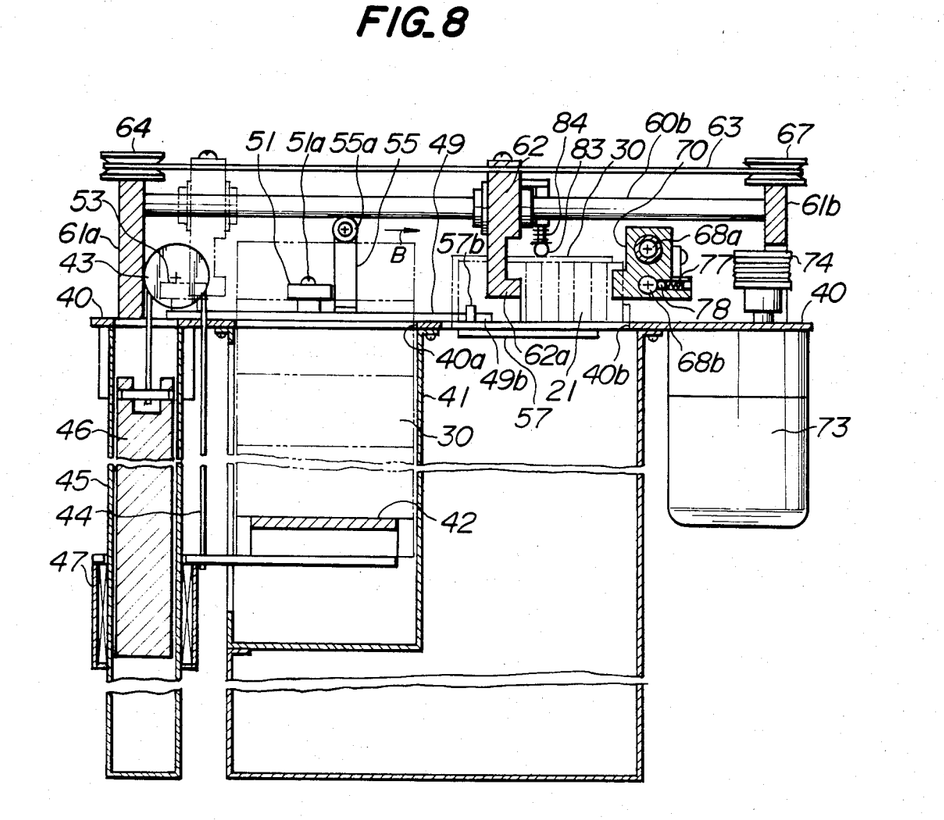
FIG. 8 is a cross sectional view illustrating the apparatus shown in FIG. 7.

FIGS. 7 and 8 illustrate an embodiment of an automatic cuvette loader according to the present invention for supplying the cuvettes 21 in the magazine 30 one by one into successive recesses 28a of the cuvette holding turntable 28. The turntable 28 is rotated in a direction C in FIG. 7 in a stepwise manner at a given frequency to form a circular reaction line.

The cuvette auto-loader comprises a base plate 40 to the lower surface of which is secured a magazine container 41 as best shown in FIG. 8. In the magazine container 41 is arranged movably up and down a magazine support 42 to which is secured one end of a wire 44 whose other end is connected via a pulley 43 to a weight 46 which is movably supported in a cylindrical guide 45. Therefore, the magazine support 42 is biased upwardly. In the magazine container 41 there may be arranged a plurality of the magazines 30 each containing a hundred cuvettes 21.

In the base plate 40 is formed a first opening 40a above the magazine container 40, the opening 40a having such dimensions that the magazine 30 can pass therethrough. On the upper surface of the base plate 40 are arranged L-shaped levers 48 and 49 rotatable about shafts 48a and 49a, respectively. To these levers are secured ring-shaped stoppers 50 and 51 by means of shafts 50a and 50b, respectively. As explained later, to the levers 48 and 49 are also secured rollers 52 and 53 by means of shafts 52a and 53a. In free ends of the L-shaped levers 48 and 49 are further formed projections 48b and 49b, respectively. Adjacent the opening 40a of the base plate 40 there are further arranged L-shaped posts 54 and 55 and stoppers 54a and 55a are secured to the posts.

In the base plate 40 there is further formed a second opening 40b through which the magazine can be passed. Beside the second opening 40b a pair of magazine support levers 56 and 57 are arranged rotatably about shafts 56a and 57a. Near free ends of these levers are secured pins 56b and 57b, respectively, these pins being engaged with the projections 48b and 49b of the levers 48 and 49, respectively. To the levers 56 and 57 are further secured pins 56c and 57c which are engaged with projections of push levers 58 and 59 which are arranged rotatably about shafts 58a and 59a, respectively extending in parallel with the plane of the drawing of FIG. 7. The levers 48, 49, 56, 57, 58 and 59 are biased by means of springs not shown into positions shown by solid lines. When the levers 56 and 57 are moved as depicted by imaginary lines, the push levers 58 and 59 are rotated in a plane perpendicular to the plane of the drawing of FIG. 7.

To the base plate 40 are further secured two guide shafts 60a and 60b by means of leg portions 61a and 61b, the guide shafts extending above the first and second openings 40a and 40b. A first slider 62 is movably secured to the guide shafts 60a and 60b by means of linear bearings. To the first slider 62 is secured a wire 63 which is wound around a pulley 64 provided on the leg portion 61a, a pulley 66 secured to a driving shaft of a motor 65 and a pulley 67 provided on the leg portion 61b. When the motor 65 is driven in both directions, it is possible to move the first slider 62 in a direction B along the guide shafts 60a and 60b in a reciprocal manner. By this movement, it is possible to transfer the magazine 30 situated above the first opening 40a into a cuvette charging position above the second opening 40b and to feed the cuvettes 21 in the magazine 30 in the direction B. For this purpose, to the lower surface of slider 62 are secured three arms 62a which can be inserted in the recesses 31f formed in the magazine 30 to contact the push plate 32.

There are further provided a pair of guide shafts 68a and 68b extending perpendicularly to the guide shafts 60a and 60b, the guide shafts 68a and 68b being coupled with the base plate 40 by means of leg portions 69a and 69b. To these guide shafts 68a and 68b is slidably mounted a second slider 70 to which is connected a wire 71 extending around a pulley 72 secured to the leg portion 69a, a pulley 74 connected to a driving shaft of a motor 73 and a pulley 75 secured to the leg portion 69b. When the motor 73 is driven in both directions, the second slider 70 can be moved reciprocally in the direction A along the guide shafts 68a and 68b. By this movement, the cuvettes 21 in the magazine 30 can be inserted into the recesses 28a of the cuvette holder 28 one by one. To this end, to the slider 70 is slidably secured a pin 70a to which a pushing claw 70c is connected and a coiled spring 70b is arranged around the pin 70a. Then, it is possible to push resiliently the cuvette 21 situating at an extreme position in the magazine 30 by means of the pushing claw 70c.

A coiled spring 76 is inserted between the guide shaft 68b and the leg portion 69a and the guide shaft 68b is slidably mounted on the leg portion 69a and therefore, the guide shafts 68a and 68b are biased in the leftward direction in FIG. 7. Further, as shown in FIG. 8, the slider 70 is slidably secured to the guide shaft 68a by means of a linear bearing, but is coupled with the guide shaft 68b in a frictional manner by means of a coiled spring 77 and a ball 78. Therefore, the slider 70 and the guide shaft 68b can be moved together over a certain limited range. To the other end of guide shaft 68b is connected an L-shaped rail supporting member 79 to which is secured a guide rail 80 having a trough construction whose width is substantially equal to the width W of the cuvette 21. The guide rail 80 is supported by guide rollers 81a to 81d and can be moved in the direction A over a relatively small distance. Near a tip of the guide rail is arranged a leaf spring 82 for pressing the cuvette situated at the tip of guide rail 80.

Now the operation of the automatic cuvette loader of this embodiment will be explained. It is assumed that in the magazine container 41 there are set several magazines 30 and the uppermost magazine is engaged with the stoppers 50 and 51 secured to the levers 48 and 49, respectively, so that the magazine stock does not move upwardly any further. Above the second opening 40b is positioned a magazine 30 which is supported by the levers 56 and 57, so that it does not fall down in the opening 40b. The magazine situating at the cuvette charging position above the second opening 40b contains a number of cuvettes 21 to be successively supplied into the respective recesses 28a of the cuvette holder 28. When the motor 73 is driven in a forward direction, the wire 71 is rotated in the clockwise direction in FIG. 7 and thus, the slider 70 is moved in the direction A. At the same time, the guide shaft 68b also is moved in the direction A and thus, the rail supporting member 79 and guide rail 80 also are moved in the direction A. During this movement, the first cuvette column (the uppermost horizontally aligned cuvettes in FIG. 7) is moved also in the direction A. The guide shaft 68b is moved in the direction A until a nut 68c provided on the right hand end of guide shaft 68b is engaged with the leg portion 69a, and after that, only the slider 70 is further moved in the direction A. By this movement of the slider 70, the cuvette column is moved in the direction A and the left hand cuvette is discharged out of the guide rail 80 and is inserted into the recess 28a of the cuvette holder 28, which recess is situated just opposite to the guide rail 80. As explained above, the cuvette 21 has the T-shaped projection 21g formed in its main wall 21b and therefore, the cuvette 21 is resiliently clamped in the recess 28a. Next the motor 73 is driven in the reverse direction and the slider 70 and guide shaft 68b are moved in a direction opposite to the direction A until the rail supporting member 79 contacts the leg portion 69b. During this reverse movement, the pushing claw 70c of the slider 70 is always in contact with the cuvette.

By repeating the above operation, successive cuvettes in the uppermost column in FIG. 7 can be supplied into respective recesses 28a of the cuvette holder 28 one by one After that the motor 73 is driven in the reverse direction and the slider 70 is returned in the right hand position in FIG. 7. Then, the motor 65 is driven in a forward direction by a predetermined amount and the wire 63 is rotated in the counter-clockwise direction in FIG. 7. During this movement, the first slider 62 is moved in the direction B by a distance equal to the width W of the cuvette 21 and the cuvettes remaining in the magazine 30 are moved in the direction B by means of the pushing plate 32.

In this manner, all the cuvettes 21 in the magazine 30 can be supplied successively into the reaction line constituted by the cuvette holder 28. After that, the motor 65 is driven in a reverse direction and the slider 62 is moved in a direction opposite to the direction B into the lowermost position in FIG. 7. At the end of this movement of the slider 62, the slider 62 is engaged with the rollers 52 and 53 on the levers 48 and 49. Then the levers 48 and 49 ar rotated into positions shown by chain lines and the ring-shaped stoppers 50 and 51 are disengaged from the magazine 30. Then the uppermost magazine in the magazine container 41 is moved above the base plate 40 through the first opening 40a and is engaged with the stoppers 54a and 55a. When the levers 48 and 49 are rotated, the arms 56 and 57 also are rotated by means of the engagement of the projections 48b and 49b with the pins 56b and 57b, into positions illustrated by chain lines, so that the empty magazine drops down through the second opening 40b. In order to enhance the operation for discharging the empty magazine from the cuvette loading position, the pushing levers 58 and 59 are rotated in conjunction with the rotation of the arms 56 and 57 so as to push the magazine downward.

Finally, the motor 65 is driven in the forward direction and the slider 62 is moved upward in FIG. 7 and the levers 48, 49, 56, 57, 58 and 59 are returned into the positions shown by solid lines. In this manner, the new magazine can be set into the cuvette loading position.

The present invention is not limited to the embodiments explained above, but may be modified in various manners. For instance, in the above embodiments a hundred cuvettes are contained in a single magazine, but any desired number of cuvettes may be contained in the magazine. Further, a single array of a plurality of cuvettes may be arranged in an elongated magazine. In such a case, it is not necessary to move the cuvettes in the direction B in the magazine. Moreover, in the above embodiment, the used cuvettes are disposed of, but they may be used repeatedly after washing them.

It should further be noted that the construction of the cuvette is not limited to that shown in FIGS. 3 and 4. For instance, the T-shaped projection 21g may be formed in both the main walls 21b and 21c. Further, legs may be provided by extending the side walls 21d and 21e beyond the bottom 21f. In this case, the outer bottom surface may also be shaped circularly corresponding to the semicylindrical inner bottom surface.

According to the invention, the reaction cuvettes can be supplied successively into the reaction line in a positive and accurate manner without staining and injuring the cuvettes, so that the reliability and accuracy of measurement can be increased materially. Further, the automatic cuvette loader has simple construction and can be made less expensively. Moreover, since the entrance and exit windows of the cuvette are effectively protected by the surrounding walls against stain, injury and stray light, the measuring precision can be made much higher. Further, a number of cuvettes are contained in the magazine and thus, the transportation and management of the cuvettes can be easily effected without staining and injuring the cuvettes. Moreover, the cuvettes may be supplemented in a prompt manner during the analysis without interrupting the measurement.

What is claimed is:

1. An automatic cuvette loading apparatus for use in an automatic chemical analyzer comprising:
   a plurality of magazines, each magazine containing a plurality of cuvette rows and each row having a plurality of cuvettes, each magazine comprising:
   (i) a top and a bottom arranged in parallel with each other;
   (ii) first and second side walls arranged in parallel with each other between opposing side edges of said top and bottom;
   (iii) third and fourth side walls arranged in parallel with each other between other opposing side edges of said top and bottom and between said first and second side walls;
   (iv) an outlet provided in the first side wall and sized to allow discharge of the cuvettes therethrough one by one;
   (v) a movable push plate contained within the magazine and being substantially parallal wlth said rows of cuvettes; and
   (vi) a window formed in ihe third side wall and extending from the first side wall to the second side wall;
   means for containing said plurality of magazines;
   means for successively feeding magazines from said magazine containing means into a cuvette loading position, said top and bottom of a magazine in said cuvette loading position being substantially horizontal;
   reaction line means for conveying cuvettes to an analyzing station located along said reaction line, said reaction line having a cuvette receiving part disposed opposite a magazine in said cuvette loading position;
   means, insertable into said magazine through said window, for successively loading the cuvettes in one cuvette row contained in the magazine situated at the ouvette loading position horizontally one by one through the outlet of the magazine into said cuvette receiving part of the reaction line;
   means for moving cuvette rows in the relevant magazine, after loading of the one cuvette row has been completed, in a direction substantially horizontal, thereby to move a new row of cuvettes to become the one cuvette row being loaded, said means for moving cuvette rows engaging said push plate to move said cuvette rows; and
   means for removing an empty magazine from the cuvette loading position.

2. An apparatus according to claim 1, wherein said magazine removing means comprises means for dropping the empty magazine down due to the gravitational force.

3. An apparatus according to claim 1, wherein each said magazine further comprises a resilient projection formed in said third side wall near said outlet to press against a cuvette being discharged through said outlet so as to ensure proper positioning of the cuvette upon discharge thereof.

4. An apparatus according to claim 1, wherein each said magazine further comprises at least one recess formed in said top and said fourth side wall such that said means for moving the cuvette rows can be inserted into the magazine through said recess.

5. An apparatus according to claim 1, wherein the top, bottom and side walls of each said magazine comprise a single integrally molded piece.

6. An apparatus according to claim 1, wherein said magazine containing means comprises a container for holding a stack of the magazines one on the other, a magazine support slidably arranged in the container and means for moving the magazine support in an upward direction.

7. An apparatus according to claim 6, wherein said magazine feeding means comprises a first slider movably arranged betwee the magazine containing means and the cuvette loading means and means for reciprocating the first slider.

8. An apparatus according to claim 7, wherein said magazine containing means further comprises stopper means for inhibiting the upward movement of the magazine stack and said stopper means is removed from the magazine stack by means of the first slider of the magazine feeding means.

9. An apparatus according to claim 8, wherein said magazine removing means is made operative in conjunction with the movement of the stopping means.

10. An apparatus according to claim 7, wherein said cuvette loading means comprises a second slider for pushing said one cuvette row to successively load the cuvettes therein and further comprises means for reciprocating the second slider so as to allow said means for moving cuvette rows to move a new cuvette row to become said one cuvette row.

11. An apparatus according to claim 7, wherein said first slider further comprises said means for moving cuvette rows.

* * * * *